United States Patent
Cheng et al.

(10) Patent No.: US 7,566,392 B2
(45) Date of Patent: Jul. 28, 2009

(54) PULSED ELECTROCHEMICAL DETECTION METHOD

(75) Inventors: Jun Cheng, San Jose, CA (US); Petr Jandik, Los Gatos, CA (US); Xiaodong Liu, Cupertino, CA (US); Christopher A. Pohl, Union City, CA (US)

(73) Assignee: Dionex Corporation, Sunnyvale, CA (US)

( * ) Notice: Subject to any disclaimer, the term of this patent is extended or adjusted under 35 U.S.C. 154(b) by 321 days.

(21) Appl. No.: 11/403,565

(22) Filed: Apr. 12, 2006

(65) Prior Publication Data

US 2007/0240998 A1  Oct. 18, 2007

(51) Int. Cl.
*G01N 27/403* (2006.01)

(52) U.S. Cl. .................. 205/775; 205/786.5; 205/787; 204/402

(58) Field of Classification Search .................. 205/775, 205/780.5, 786.5, 787, 789; 204/402, 403, 204/409; 73/61.58
See application file for complete search history.

(56) References Cited

U.S. PATENT DOCUMENTS

| | | | |
|---|---|---|---|
| 4,939,924 | A | 7/1990 | Johnson et al. |
| 5,403,451 | A | 4/1995 | Riviello et al. |
| 6,478,950 | B1 * | 11/2002 | Peat et al. .................. 205/775 |
| 6,514,762 | B1 | 2/2003 | Wang |
| 6,931,327 | B2 | 8/2005 | Goode et al. |
| 2005/0067304 | A1 * | 3/2005 | King et al. .................. 205/794 |

OTHER PUBLICATIONS

Alciaturi, C., et al., "On the anodic oxidation of cyclohexene on platinized platinum electrodes," *Electrochim. Acta* 25(3):353-355 (Mar. 1980).

Alciaturi, C., et al., "Partial oxidation of butadiene on platinized Pt and Au anodes in acid aqueous solutions," *Electrochim. Acta* 25(3):357-363 (Mar. 1980).

Andreescu, S., et al., "A new electrocatalytic mechanism for the oxidation of phenols at platinum electrode," *Electrochem. Comm.* 5(8):681-688 (Aug. 2003).

Austin, D., et al., "Electrocatalysis at platinum electrodes for anodic electronanlysis," *J. Electroanal. Chem.* 168(1-2):227-248 (May 1984).

Bagotzky, V., et al., "generalized scheme of chemsorption, electroxidation, and electroreduction of simple organic compounds on platinum group metals," *J. Electroanal. Chem.* 81(2):229-238 (Aug. 1977).

Baranski, A., et al., "Voltammetric determination of surface active compounds at Au and Pt unltramicroelectrodes in flow solutions," *Can. J. Chem.* 75(11):1736-1749 (Nov. 1997).

(Continued)

*Primary Examiner*—Kaj K Olsen
(74) *Attorney, Agent, or Firm*—Morgan, Lewis & Bockius LLP; David J. Brezner; Victor E. Johnson (57) ABSTRACT

In one embodiment, the present invention is directed to a pulsed electrochemical detection method comprising (a) flowing a liquid sample stream including at least one analyte past a working electrode in a flow-through cell; (b) applying at least three pulsed electrical potentials to the working electrode, (1) a first conditioning potential, (2) a second detection and oxidative cleaning potential, and (3) a third reductive cleaning potential, said second potential being higher than said first and third potentials and said first potential being higher than said third potential; and (c) detecting the output from said working electrode during the time period of applying said second potential.

14 Claims, 7 Drawing Sheets

OTHER PUBLICATIONS

Beltowska-Brzezinska, M., et al., "Electrocatalytic oxidation of mono- and polyalcohols on gold and platinum," *J. Appl. Electrochem.* 27(9):999-1011 (Sep. 1997).

Beltowska-Brzezinska, M., et al., "Ethylene oxidation and hydrogenation on porous Pt electrode in acidic solution," *J. Electroanal. Chem.* 519(1-2):101-110 (Feb. 2002).

Burke, L., et al., "Multilayer oxide growth on Pt under potential cycling conditions—II $HClO_4$ and NaOH solutions," *Electrochim. Acta* 37(1):43-50 (Jan. 1992).

Casella, I., et al., "Determination of aliphatic aldehydes by liquid chromatography with pulsed amperometric detection," *J. Chromatogr. A* 1063(1-2):129-135 (Jan. 2005).

Casella, I., et al., "Determination of aliphatic organic acids by high performance liquid chromatography with pulsed amperometric detection," *J. Agri. Food Chem.* 50(1):23-28 (Jan. 2002).

Dionex Corp., "Determination of sulfite in food and beverages by ion exclusion chromatography with pulsed amperometric detection," *Application Note* 54 (1999).

Dionex Corp., "Ion chromatography: a versatile technique for the analysis of beer," *Application Note* 46 (1997).

Fanguy, J., et al., "Pulsed amperometric detection of carbohydrates on an electrophoretic microchip," *Analyst* 127(8):1021-1023 (Aug. 2002).

Fanguy, J., et al., "The analysis of uric acid in urine using microchip capillary electrophoresis with electrochemical detection," *Electrophoresis* 23(5):767-773 (Mar. 2002).

Goncharuk, V., et al., "Electrokinetic oxidation of phenol on a stationary platinum electrode," *Soviet J. Water Chem. Tech.* 6:51-55 (1984).

GRAβ, B., et al., "Comparison of different conductivity detector geometries on an isotachophoresis PMMA-microchip," *Anal. Bioanal. Chem.* 371:228-233 (2001).

Hughes, S., et l., "Amperometric detection of simple alcohols in aqueous solutions by applications of a triple-pulse potential waveform at platinum electrodes," *Anal. Chim. Acta* 132:1-10 (Dec. 1981).

Jirovský, D., et al., "Analysis of phenolic acids in plant materials using HPLC with amperometric detection at a platinum tubular electrode," *J. Sep. Sci.* 26(8):739-742 (Jun. 2003).

Johll, M., et al., "Activated pulsed amperometric detection of cysteine at platinum electrodes in acidic media," *Electroanalysis* 9:1397-1342 (1997).

Johnson, D., et al., "Anodic detection in flow-through cells," *J. Chem. Soc. Faraday Transact.* 1 82(4):1081-1098 1986.

Johnson, D., et al., "Liquid chromatography with pulsed amperometric detection at gold and platinum electrodes," *Anal. Chem.* 62(6):589A-597A (Mar. 1990).

Johnson, D., et al., "Pulsed amperometric detection of carbohydrates amines and sulfur species in ion chromatography—the current state of research," *J. Chromatogr. A* 640(1-2):79-96 (Jun. 1993).

Koile, R., et al., "Electrochemical removal of phenolic films from a platinum anode," *Anal. Chem.* 51(6):741-744 (May 1979).

LaCourse, W., et al., "Pulsed amperometric detection of aliphatic alcohols in liquid chromatography," *Anal. Chem.* 63(2):134-139 (Jun. 1991).

Nonaka, H., et al., "Electrochemical oxidation of carbon monoxide, methanol, formic acid, ethanol, and acetic acid on a platinum electrode under hot aqueous conditions," *J. Electroanal. Chem.* 520(1-2):101-110 (Feb. 2002).

Ogibin, Y., et al., "Electrochemical reactions of alkene induced by anodic oxidation and their applications in organic synthesis," *Russ. Chem. Rev.* 70(7):543-576 (2001).

Parsons, R., et al., "The oxidation of small organic molecules: a survey of recent fuel cell related research," *J. Electroanal. Chem.* 257(1-2):9-45 (Dec. 1988).

Rocklin, R., et al., "Ion chromatography with pulsed amperometric detection: simultaneous determination of formic acid, formaldehyde, acetaldehyde, propionaldehyde, and butyraldehyde," *Adv. Chem. Series* 210:13-21 (1985).

Salavagione, H., et al., "Spectrochemical study of the oxidation of aminophenols on platinum electrode in acid medium," *J. Electroanal. Chem.* 565(2):375-383 (Apr. 2004).

Samcová, E., et al., "Determination of urinary 8-hydroxy-2-deoxyguanosine in obese patients by HPLC with electrochemical detection," *Anal. Chim. Acta* 516(1-2):107-110 (Jul. 2004).

Snell, K., et al., "Effect of anions and pH on ethanol electroxidation at a platinum electrode," *Electrochim. Acta* 27(12):1683-1696 (Dec. 1982).

Štulík, K., et al., "Electrochemical detector for high-performance liquid chromatography," *J. Chromatogr.* 192:135-141 (Apr. 1980).

Takahashi, A., et al., "Determination of hydrogen peroxide by high-performance liquid chromatography with a cation-exchange resin gel column and electrochemical detector," *Anal. Sci.* 15(5):481-483 (1999).

Tarnowski, D., et al., "Amperometric detection with membraned-based sampling for percent-level determination of ethanol," *Anal. Chim. Acta* 332(2-3):111-121 (Oct. 1996).

vam Riel, J., et al., "Selective detection of RP-HPLC of Tyr-, Trp- and sulfur-containing peptides by pulsed amperometry at platinum," *Anal. Chem.* 67(21):3911-3915 (Nov. 1995).

Wygant, M., et al., "Improved in amperometric detection of sulfite in food matrices," *J. AOAC Intl.* 80:1374-1380 (1997).

Zelenay, P., et al., "The inhibitory effect of some surface active organic compounds on the electroxidation of strongly absorbed species derived from HCOOH on polycrystalline platinum," *J. Electroanal. Chem.* 176(1-2):209-224 (Sep. 1984).

Zhao, C., et al., "Determination of L-cysteine in amino acids mixture and human urine by flow-injection analysis with a biamperometric detector," *Anal. Biochem.* 29(2)7:170-176 (Oct. 2001).

\* cited by examiner

Det.: 0.30 V
Int. Time: 0.02 s
LOD: NA

Det.: 1.15 V
Int. Time: 0.10 s
LOD: 53 µM (Peak 4)

CH$_3$COCH$_3$   CH$_3$COCH$_2$CH$_3$

Column: IonPac® ICE-AS1 (4 x 250 mm)
Temp.: 30 °C
Eluent: 100 mM MSA
Flow Rate: 0.20 mL/min
Inj. Vol.: 20 µL
Det. Met.: PAD (Detailed conditions as specified)
Electrode: Disposable Pt (1 mm)
Gasket Thickness: 2 mil
Reaction Coil: 375 µL
Samples: Ketones (10 mM)

Peaks:
1. Exclusion Volume
2. Impurity
3. Acetone
4. 2-Butanone

FIG. 4

Column: IonPac® ICE-A1 (4 x 250 mm)
Temp.: 30° C
Eluent: 100 mM MSA
Flow Rate: 0.20 mL/min
Inj. Vol.: 20 μL
Det. Met.: PAD (Int. at E1 or E2)
Electrode: Disposable Pt (1 mm)
Gasket
Thickness: 2 mil
Sample: Formaldehyde Standard Peaks:
1. Exclusion Volume
2. Formaldehyde       100 μM
3. Oxygen             NA

FIG. 5

Column: IonPac® ICE-AS1 (4 x 250 mm)
Temp.: 30° C
Eluent: 100 mM MSA
Flow Rate: 0.20 mL/min
Inj. Vol.: 20 μL
Det. Met.: PAD (Int. at E1 or E2)
Electrode: Disposable Pt (1 mm)
Gasket
Thickness: 2 mil
Reaction
Coil: 375 μL
Sample: Sulfite Standard Peaks:
1. Exclusion Volume
2. Stabilizer         NA
3. Sulfite            10 ppm

FIG. 6

Background Noise ( nC ): 0.3567 (E1), 0.0286 (E2);
Peak Area ( nC.min , peak 6): 6.68 (E1), 2.24 (E2);
Limit of Detection ( ppm ): 4.64 (E1), 1.09 (E2).

Column: IonPac® ICE-AS1 (4 x 250 mm)
Temp.: 30 ° C
Eluent: 100 mM MSA
Flow Rate: 0.20 mL/min
Inj. Vol. : 20 µL
Det. Met.: PAD (Int. at E1 or E2)
Electrode: Disposable Pt (1 mm)
Gasket Thickness: 2 mil
Reaction Coil: 375µL
Sample: Standards of Alcohols

Peaks:
1. Exclusion Volume
2. Sorbitol          50 ppm
3. Glycerol          50
4. Ethylene glycol   50
5. Methanol          50
6. Ethanol           50
7. 1-Propanol        50
8. 1-Butanol         100

| Column: | IonPac® ICE-AS1 (4 x 250 mm) |
|---|---|
| Temp.: | 30 °C |
| Eluent: | 100 mM MSA |
| Flow Rate: | 0.10 mL/min |
| Inj. Vol.: | 20 µL |
| Det. Met.: | PAD (Int. at E2) |
| Electrode: | Disposable Pt (1 mm) |
| Gasket Thickness: | 2 mil |
| Reaction Coil: | 375 µL |
| Sample: | Propionic and Acrylic Acids (100 µM) |

Peaks:
1. Exclusion Volume
2. Propionic Acid         100 µM
3. Acrylic Acid           100
4. Impurity

FIG. 12

PULSED ELECTROCHEMICAL DETECTION METHOD

BACKGROUND OF THE INVENTION

Direct electrochemical detection of aliphatic compounds with electroactive functional groups based on electrocatalytic reactions at noble metal electrodes, chiefly Au and Pt, is well known. Electrochemical detection is a widely accepted means of detection in liquid and ion chromatography. Electrochemical detectors operate by applying an electrical potential to the working electrode in a flow-through cell. Such detectors typically employ a cell of three electrodes, which are a working electrode, a reference electrode and a counter electrode. Typically, the methodology uses multi-step potential waveforms which incorporate a detection operation along with the anodic and cathodic cleaning of the electrode surface. In a typical potential waveform, anodic detection occurs at a first potential with current sampling at the end of the time period of applying the potential. The potential then is stepped to a second higher potential for oxidative cleaning of the electrode surface, and subsequently to a third potential lower than the first or second potentials for cleaning by cathodic dissolution of the surface oxide formed at the first and/or second potentials. An analytical application of this method using amperometric detection, now known as Pulsed Amperometric Detection (PAD), has been demonstrated for alcohols, polyalcohols and carbohydrates (reducing and non-reducing); amines and amino acids (primary and secondary); aminoglycosides; and numerous sulfur compounds (except sulfate, sulfonic acids and sulfones).

Pulsed Coulometric Detection (PCD) has been described. The significant difference between PAD and PCD lies in the instrumental protocol related to measurement of the detection signal. The term "pulsed electrochemical detection" or "PED" is a general term that encompasses PAD and PCD. In PAD, electrode current is sampled or averaged over a time period (e.g., 16.7 ms) (at $\frac{1}{60}$ $Hz^{-1}$) whereas in PCD the response is electronically integrated over a single period or over an integral number of sequential periods. PCD inherently has a larger signal-to-noise ratio (S/N) because of the larger signal strength and because the integral of a 60-Hz correlated noise signal, a predominant form of noise in electronic instrumentation, remains at zero over the integration period.

Photometric detection suffers because of an inherently low sensitivity for aliphatic compounds without extensive π-bonding and because of baseline drift which accompanies a change in the refractive index of the mobile phase. Refractive index detection is strongly affected by concentration gradients and the baseline shift observed for even small changes in mobile phase composition can overwhelm the analyte signal.

The methods of PAD and PCD were introduced for detection of numerous aliphatic organic compounds with electroactive functional groups in conjunction with liquid chromatography (LC). Numerous PAD/PCD methods have become part of daily routine in academic and industrial laboratories. The majority of such methods utilize gold as a material for the working electrodes. The usage of platinum working electrodes has fallen behind the utilization of gold electrodes. Many analysts have found existing platinum-electrode based methods more difficult to use and less reproducible than those using gold electrodes.

Many analytes are detectable with working electrodes made of different materials. Various electrode materials exhibit different performance in response to sample matrix accompanying the analytes of interest. Example 1: Alcohols are detectable with platinum and gold electrodes. If alcohols are present in samples with high concentrations of sugars, platinum electrodes are preferable because they are less affected by excessive levels of sugars than gold electrodes. Example 2: Cyanide anion can be detected either with a silver electrode or with a platinum electrode. In samples with a high concentration of sulfides, silver electrodes are easily affected and have been observed to lose any response to cyanide after very few injections of high sulfide samples. Platinum electrodes are much more robust in comparison and keep providing detection response to cyanide even after many injections of high sulfide samples. Consequently, there is a need to provide more reproducible electrochemical platinum-based methodology suitable for an expanded list of analytes and which can be performed with high S/N.

SUMMARY OF THE INVENTION

In one embodiment, the present invention is directed to a pulsed electrochemical detection method comprising (a) flowing a liquid sample stream including at least one analyte past a working electrode in a flow-through cell; (b) applying at least three pulsed electrical potentials to said working electrode, (1) a first conditioning and detection potential, (2) a second detection and oxidative cleaning potential, and (3) a third reductive cleaning potential, said second potential being higher than said first and third potentials and said first potential being higher than said third potential; and (c) detecting the output from said working electrode during at least part of the time period of applying said second potential.

DETAILED DESCRIPTION OF THE INVENTION

The present invention is directed to pulsed electrochemical detection methods. In one embodiment, the detection is performed by a current integration, known as Pulsed Coulometric Detection (PCD). In another embodiment, the detection is performed amperometrically, commonly known as Pulsed Amperometric Detection (PAD). The present description will refer to these two forms of detection as electrochemical detection unless otherwise specified. An important aspect of the invention is that the output from the working electrodes for detection, e.g., by PCD or PAD, is detected during the time period applying the highest potential of the cycle. In a specific embodiment, at least three different pulsed potentials are applied to the working electrode. The first pulse is a conditioning potential, the second is a detection and oxidative cleaning potential and the third is a reductive cleaning potential. In a preferred embodiment, the second potential is higher than the first and third potentials and the first potential is higher than the third potential. The output from the working electrode is measured during the time period applying the second potential. Thus, the output signal is detected during the highest potential in a pulsed waveform of applying the potential.

Figure 1A:
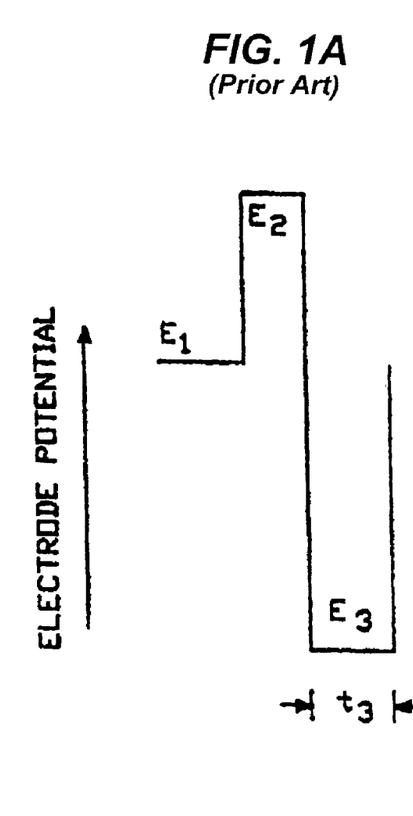
FIGS. 1A, 1B, and 1C show three (A, B, C) representative potential waveforms useful for the invention.
Figure 1B:
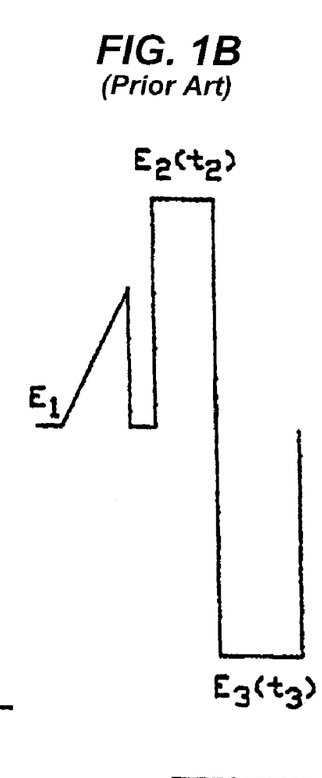
Figure 1C:
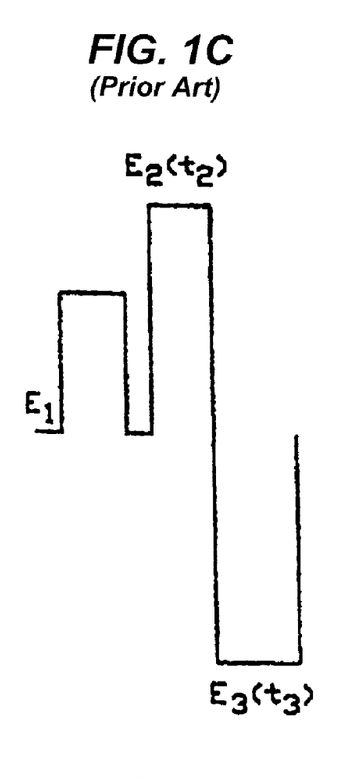

By way of illustration, the conditioning potential in FIGS. 1A, 1B, and 1C is illustrated in U.S. Pat. No. 4,939,924 which include waveforms and for purposes of the present invention $E_1$ as the conditioning potential, $E_2$ as the detection and oxidative cleaning potential, and $E_3$ as the reductive cleaning potential. An important difference between the method set forth in the '924 patent and the present invention is that the detection that takes place at the highest potential or $E_2$ in the illustrated figures.

Figure 2:
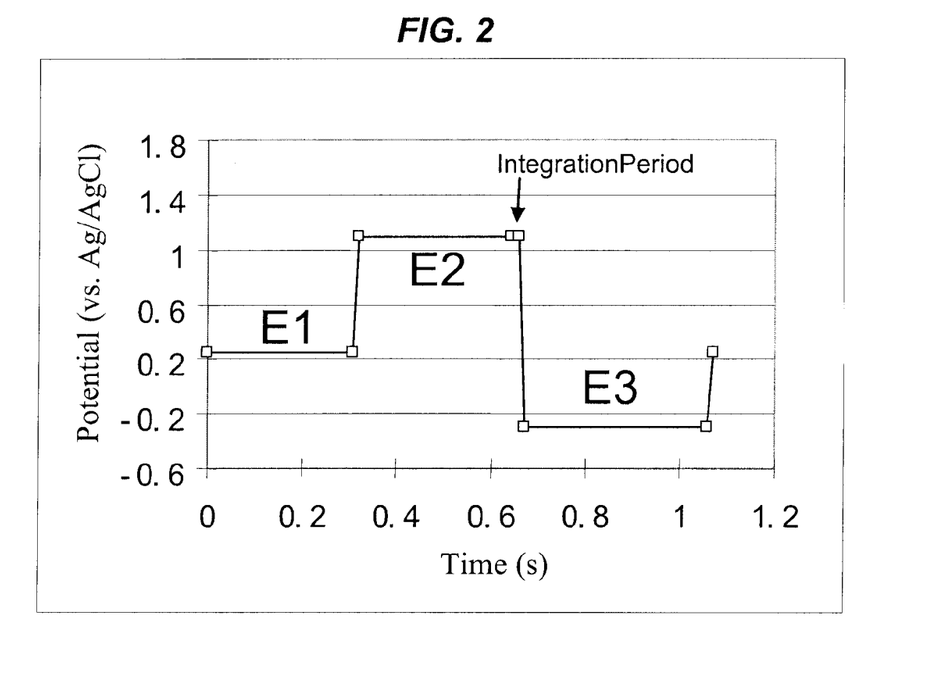
FIG. 2 illustrates a suitable stepped triple-potential waveform with an integration time period at $E_2$.

A suitable stepped triple-potential waveform with an integration time period at $E_2$ is illustrated in FIG. 2. All the potentials in the invention are reported against a reference electrode Ag/AgCl/3 M KCl.

The first conditioning potential $E_1$, which is lower than the second detection and oxidative cleaning potential and higher than the third reductive cleaning potential, serves to condition or activate the surface of the working electrodes for detection. In many cases, analytes of interest are undergoing a preadsorption at the electrode surface during the electrode conditioning. Typically the electrode surface is metal. Conditioning or activation is accomplished by formation of hydroxide radicals on the metal surface of the electrode or by creation of incomplete monolayers of metal oxides. The hydroxide radicals and freshly created small amounts of oxide are the key elements of catalytic conditions required for oxidative detection of many of organic and inorganic compounds at metal electrodes.

At the second or detection and oxidative cleaning potential, the surface of the electrode typically is still covered by the catalysts (radicals and/or oxides). The catalysts are essentially unstable oxygen compounds making oxygen available in the close proximity to pre-adsorbed analytes. The analytes of interest are being pre-adsorbed either during the conditioning step or during the detection step. Frequently, their pre-adsorption stretches over both steps. As the adsorbed analytes encounter the catalytic sites, oxidative desorption takes place producing electrons which are being detected as a signal. At the potential $E2$, the rate of the electrode reaction becomes more independent of adsorption rates than at the potential $E1$. The increased independence of the adsorption rates considerably improves the linearity of detection. Concurrently with the oxidative desorption producing the detection signal, the electrode surface coverage by the oxide typically increases. More stable, less catalytic oxides tend to become predominant, especially if an excessively long time period is selected for the $E2$ potential. In contrast, the prior art detection (PAD or PCD) takes place at the potential $E1$ where the rate of oxidative desorption is to a much larger degree controlled by the rate of adsorption and in consequence the linearity of calibration plots is inferior, especially in the case of platinum electrodes.

At the third cleaning reductive potential $E_3$, the working electrode surface is freed of all oxygen species created during the conditioning and detection periods. Simultaneous with the removal of oxides, last remnants of adsorbed analytes and/or their oxidation products, which may have been trapped beneath excessive amounts of non-catalytic oxides, typically are also removed.

The present system can be used for detecting analytes in a liquid sample stream. It is applicable to flow injection analysis (FIA) for detecting one or more analytes in a liquid sample stream. It is particularly useful for detection of analytes in a liquid sample stream which have been previously separated through separation medium such as in a chromatographic column. The separated analytes are detected at the working electrode.

The potential waveform may be a potential step function which is constant during one or more of the three potential pulses or may be in any other form such as a potential sweep function so long as the relative potential levels of the three pulses are as set forth above.

By detection at the highest potential, the level of noise can be minimized and the range of linear calibration can be extended for a number of different analytes. Further, detection at the highest potential would move the signal detection from a range of oxygen reduction to hydrogen peroxide around 0.47 V on the electrodes. Because of that, baseline pulsations and oxygen dip may be eliminated or minimized. Further, the lower potentials of conditioning and cleaning can be optimized without regard to performance during detection. Thus, for example, analyte preadsorption or surface-preconditioning can be optimized at E1 and E3 of the waveform potential prior to detection. Another advantage is that the linearity of calibration is improved for many analytes. Furthermore, some new categories of analytes can be detected, such as ethers and ketones.

Suitable ranges of potentials and times for PED waveforms with platinum electrodes include:

|    | Potential [V] vs. AgAgCl | Time [s]  |
|----|--------------------------|-----------|
| E1 | −0.10-0.80               | 0.10-1.0  |
| E2 | 0.90-1.80                | 0.10-1.0  |
| E3 | −1.00-0.00               | 0.10-1.0  |

Preferred ranges of potentials and times for PED waveforms with platinum electrodes include:

|    | Potential [V] vs. AgAgCl | Time [s]  |
|----|--------------------------|-----------|
| E1 | 0.20-0.50                | 0.30-0.50 |
| E2 | 1.10-1.30                | 0.20-0.40 |
| E3 | −0.20--0.50              | 0.50-0.70 |

The detection period may take place during the entire time for applying the second potential, E2 for PED. However, it is preferable to detect only for the last 5%-90%, more preferably the last 10%-30% of the period for apply E2.

The invention has been described with respect to a pulsed electrochemical detection method including at least a first conditioning potential, a second detection and oxidative cleaning potential and a third reductive cleaning potential. It also encompasses systems which include the application of additional potentials before, after, or between the application of these potentials so long as the potential and detection relationship of the above three potentials set forth herein is present.

The system of the present invention is particularly effective for a working electrode in an exterior surface formed of a metal material such as platinum, iridium, palladium, rhodium, ruthenium, and lead. A preferred working material electrode is platinum.

One theoretical explanation of why the detection method of the present invention produces the foregoing advantages, particularly for the foregoing working electrodes is as follows. The choice of a relatively high potential removes the signal generation from the potential range of oxygen reduction to hydrogen peroxide. The artifacts such as "oxygen dip" or baseline pulsation stemming from sudden or periodic fluctuations of oxygen concentration in the eluent typically are thus eliminated. An additional advantage is gained by monitoring the signal producing oxidative desorption at the highest of potentials. The signal producing electrode reaction is no longer controlled by the rate of adsorption to the same degree as at the lower potentials. The range of linear calibration is expanded as a result.

The electrochemical detection method of the present invention is particularly effective for analytes such as inorganic anions, alcohols, sulfur amino acids, thioethers, sulfoxides, phenols, ethers, aldehydes, ketones, alkenes, alkynes, nitriles, amino acids, carboxylic acids and combinations thereof.

Typical potential waveforms for PCD and PAD are shown in FIGS. 1A, 1B, and 1C as illustrated in U.S. Pat. No. 4,939,924 ("the '924 patent"). In PCD or PAD, the initial value of $E_1$ is chosen so that the electrode surface exists in an oxide-poor state (formation of an incomplete monolayer of oxide). Following a delay time of $t_d$, the potential is advanced to the value $E_{1'}$ (or any number of potentials having a value $E_{1''}$, $E_{1'''}$, $E_{1''''}$ etc. <$E_2$), by a fast potential sweep (FIG. 1B) or a potential step (FIG. 1C) for a time period of $t_s$. The value of $E_{1'}$ (or $E_{1''}$, $E_{1'''}$, $E_{1''''}$, etc.) is chosen to cause the formation of surface oxide with the concurrent electrocatalytic oxidative reaction of soluble and/or adsorbed analyte. The potential then is either changed to $E_2$ or is returned to the initial value $E_1$ for the holding period $t_h$ during which all oxide formed during the potential change to $E_1$ is cathodically stripped from the electrode surface. The total time of the waveform period is the sum of the times of application of $E_1$, $E_2$ and $E_3$. An integrator (analog or digital) is activated during period of application of $E_1$ (or $E_{1'}$) and remains active throughout period of its application. The output signal from the integrator is sampled at the end of the detection period and the value, or a proportional value, is fed to a recording device. Thereafter, positive and negative pulses can be applied such as $E_2$ and $E_3$ which achieve anodic and cathodic cleaning, respectively. The integrator is reset to zero at the end of the application of $E_1$. The value(s) $E_{1'}$ is (are) chosen to maximize the extent of oxidative reaction of soluble and absorbed analyte. However, the highest potential should not be so large positive to cause significant anodic solvent breakdown with evolution of $O_2$.

For the PCD waveforms in FIGS. 1B and 1C of the '924 patent, the values of $E_1$ and the time can be sufficiently large to provide complete oxidative cleaning of the electrode and a subsequent step to $E_2$ for further oxidative cleaning may not be needed.

In general, the present invention is applicable to the measurement of irreversible electrochemical processes related to analytes of interest superimposed or coincident with other irreversible or reversible processes. The measurement of surface-oxide catalyzed reactions during the formation of surface oxide is a single example of the PCD and/or PAD technique.

As described herein, the highest potential PCD or PAD method of the present invention is particularly applicable to detection of multiple chemical components in a liquid sample which have been separated by liquid chromatography, particularly high performance liquid chromatography (HPLC). The liquid sample is normally mixed with an eluent including an electrolyte as a developing reagent and passed through a chromatography column. The packing for the column typically would include gel or particulate forms of ion exchange or reverse phase packing. The technology is well developed. For example, see C. F. Simpson, Techniques of Liquid Chromatography, 1983, J. H. Knox, High Performance Liquid Chromatography, 1981, and K. Polkar et al., Liquid Chromatography in Clinical Analysis, 1981.

In addition, the PCD method is useful as a method of detection in flow injection analysis (FIA). Such systems are described in Skeggs, Amer. J. Clin. Path., 28, 311-322 (1957) and in U.S. Pat. Nos. 4,013,413, 4,022,575, 4,177,677, 4,224,033, 4,227,973, 4,314,824, 4,315,754, 4,352,780, 4,399,102, 4,399,225, and 4,504,443. In such systems, these samples are supplied to the detector in a continuous liquid carrier flow rather than by being separated, e.g., in liquid chromatography. This technique is of limited application in comparison to the aforementioned liquid chromatographic system.

The pulsed electrochemical detection method of the present invention applies to the use of a two-electrode cell including a reference electrode and a working electrode and of a three-electrode cell including a reference electrode, a working electrode, and a counter electrode.

EXPERIMENTAL SECTION

Chemicals

Suitable solutions may be prepared from Reagent Grade Chemicals (Fisher Scientific, Fair Lawn, N.J.) and purified water (NANOpure II, Barnlsted Co., Boston Mass.

Instrumentation

Suitable instrumentation for the electrochemical method of the present invention may be of the type set forth in the '924 patent.

The sample volumes injected may be 0.1-200 μl and the flow rate was 0.0001-5.000 ml min$^{-1}$. The electrochemical flow-through cell may be of the "thin-layer" design (Dionex Corporation, Sunnyvale, Calif.) with a Pt electrode (ca. 0.0078 cm$^2$). A manufacturer supplied Ag/AgCl electrode was used in all experiments.

Procedures

All PED waveforms of FIG. 1 including the potential sweep from $E_1$ to $E_{1'}$ in waveform of FIG. 1B may be programmed either directly in the Dionex ED50 detector or created in the Chromeleon software and downloaded to the detector during the execution of a chromatographic program.

Limits of Detection and Analytical Calibration

There are two main methods for estimating limits of detection. In the first of the two methods, an average value of baseline noise is determined over a specified period of time and calibrated in concentration units with the help of an injection of known amount of analyte of interest. In the majority of cases, a three-fold multiple of baseline noise expressed in concentration or amount units is specified as a limit of detection. In the second of the two methods, the operator determines a standard deviation in concentration or amount units of a series (n>3) of injections of a single standard of known concentration. The limit of detection is then expressed as a multiple of the calculated standard deviation. The multiplication factor is derived from a selected level of confidence and can be obtained from statistical tables. Analytical calibration is generated from injections of series of standards of different concentrations. The concentration range must be selected to be greater than the expected range of unknown concentrations. From the analytical response to known concentrations of standards, a calibration plot illustrating the dependence of analytical response on concentrations, is constructed. It is well known that linear calibration plots indicate better precision and accuracy than non linear calibration plots.

Effect of Oxygen

Using the conventional approach of signal integration at $E1$, unequal concentrations of oxygen in the injected samples and in the mobile phase can give rise to a substantial artifact called "oxygen dip." The oxygen dip is caused by a detection signal due to reduction of dissolved oxygen to hydrogen peroxide at the surface of the working electrode. In the majority of cases, the concentration of oxygen is higher in a sample than in the chromatographic mobile phase. Higher concentration of oxygen results in a greater value of negative current. This is manifested in the chromatograms as a sizeable change of baseline level in the negative direction. Depending on the chromatographic conditions, the resulting baseline disturbance can extend over several minutes. A reproducible detection of the beginning and end of a chromatographic peak depends on low baseline noise and absence of baseline excursions which are not caused by the analytes of interest. If platinum electrodes are used for chromatographic detection, the oxygen dip, if present, is frequently co-eluting with and distorting the shape of important analytes (e.g. methanol and ethanol).

Comparison of Waveforms

The optimization of the waveforms for PCD, e.g., choice of FIG. 1A or 1B vs. FIG. 1C, is influenced by the analyte(s) of interest. For analytes whose detection is inhibited by formation of surface oxide, e.g., alcohols, the waveform depicted in FIG. 1C may not be considered appropriate because the stepwise change of potential from $E_1$ to $E_2$ results in the rapid and extensive formation of oxide with cessation of analytical response. Adsorbed analytes detected by mechanisms which are catalyzed by formation of surface oxide, e.g., sulfur compounds, are expected to be detected well by either waveform. As was the case for many other analytes, ketones and ethers also are detected by processes which are catalyzed by the formation of the surface oxides. The chromatograms in FIGS. 3B and 12 were obtained using the waveform of FIG. 2.

To illustrate the present invention, the following non-limiting examples of its practice are provided.

EXAMPLE 1

Figure 3A:
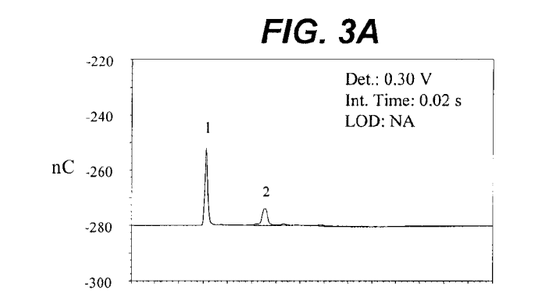
FIG. 3A shows a failed attempt to detect acetone and butanone by the prior art method (signal integration at 0.25 V)
Figure 3B:
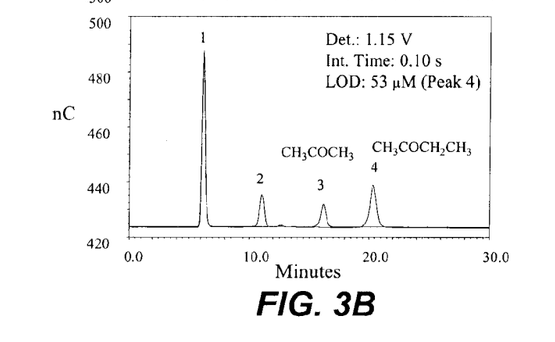
FIG. 3B shows an attempt of detecting both ketones using the same waveform but with a signal integration at E2=1.15 V.

New Method Detects a Compound Class which was Undetectable by the Prior Art Methodology FIG. 3A shows a failed attempt to detect acetone and butanone by the prior art method (signal integration at 0.25 V). Only an unknown impurity, most likely an alcohol (peak 2) generates a detection response. Using the same waveform but with a signal integration at $E2=1.15$ V (FIG. 3B) both ketones are detected easily.

EXAMPLE 2

Elimination of Oxygen Dip

Figure 4:
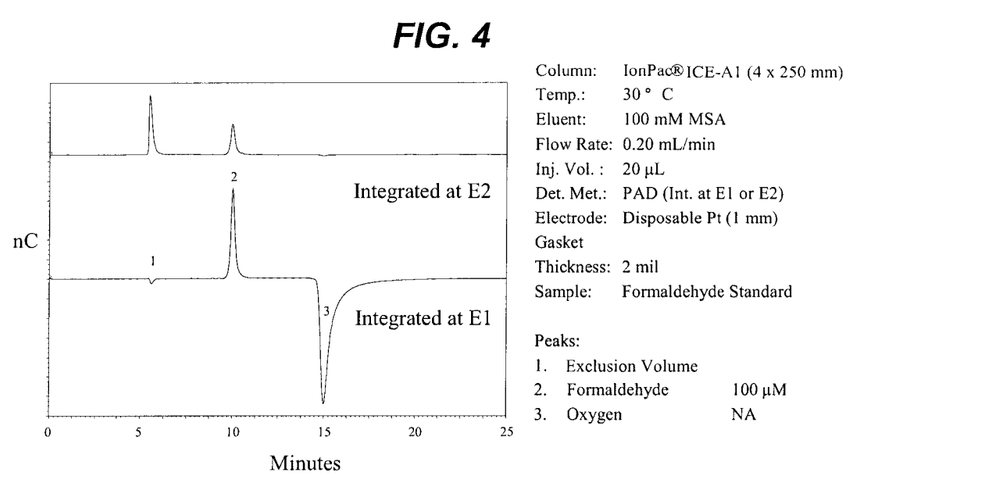
FIG. 4 shows a chromatogram exhibiting "oxygen dip" (negative peak 3, lower trace), and the new method (upper trace) minimizing oxygen dip.

Using the prior art methodology, many chromatograms exhibit a feature called "oxygen dip" (negative peak 3, lower trace). Referring to FIG. 4, the new method (upper trace) minimizes the oxygen dip by signal integration at a potential which is far removed from the potential range of oxygen reduction to hydrogen peroxide. Even though the peak height of formaldehyde has been reduced by the new method (from 46 to 15 nC), the concurrent lowering of baseline noise (from 0.125 to 0.034 nC) improved the detection limit from 0.82 to 0.66 µM by the new method.

EXAMPLE 3

Minimizing Pulsations by the New Method

Figure 5:
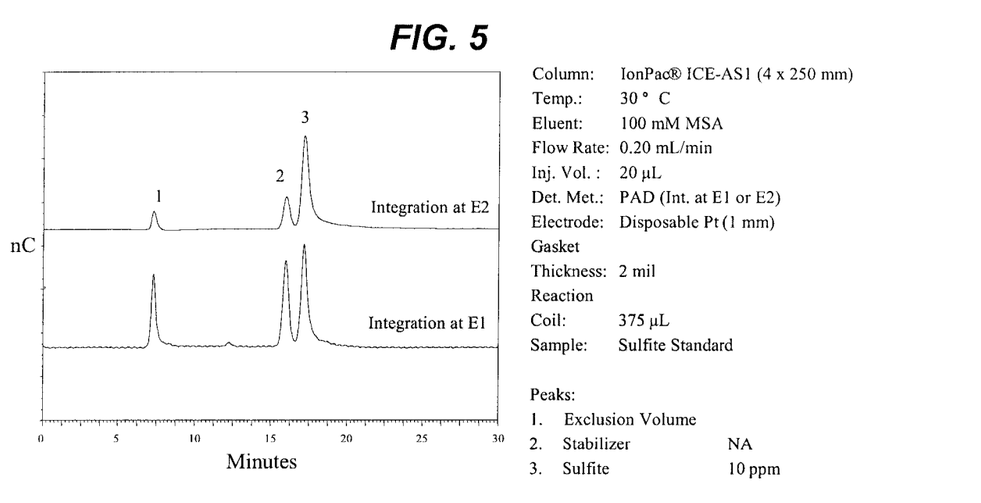
FIG. 5 shows the prior art approach and the new method generating a comparable size of response for sulfite anion (45 vs. 41 nC).

Referring to FIG. 5, the prior art approach and the new method generate a comparable size of response for sulfite anion (45 vs. 41 nC). However, the new methodology minimizes the regular baseline pulsations caused by oxygen insertion into the eluent flow by the pump pistons. The corresponding reduction in baseline noise (from 0.5 to 0.03 nC) leads to a marked improvement in the detection limits with the new method (from 0.34 to 0.02 ppm).

EXAMPLE 4

Sensitivity Improvement by Lower Noise

Figure 6:
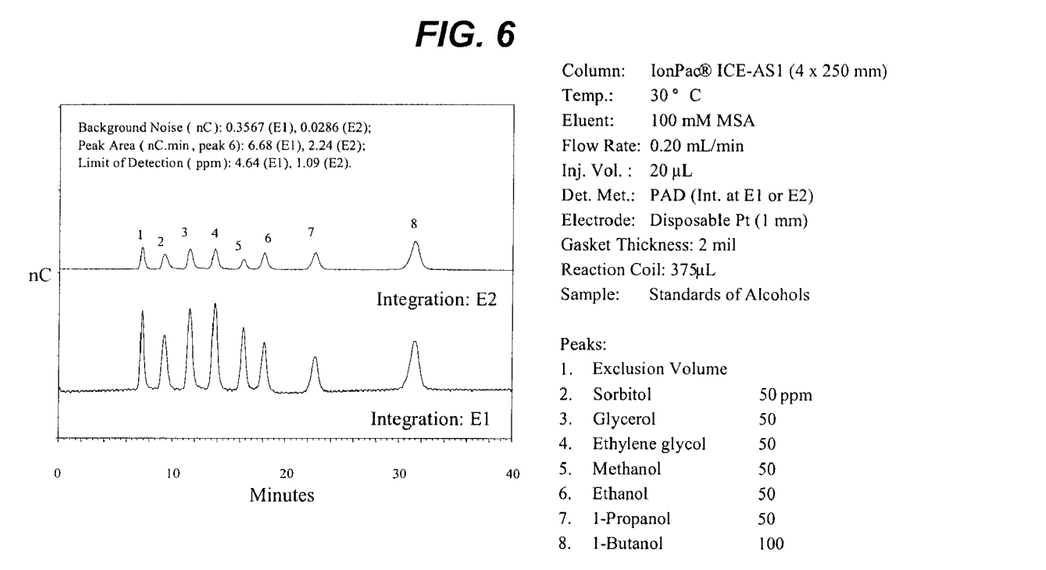
FIG. 6 shows the detection of seven different alcohols by the prior art method in the lower trace, and a chromatogram obtained with the improved methodology (Integration: E2).

Detection of seven different alcohols by the prior art method is shown in the lower trace of FIG. 6 (Integration: $E1$). The upper trace of FIG. 6 is a chromatogram obtained with the improved methodology (Integration: $E2$). The peak heights are actually somewhat lower with the improved method in this particular application example. However, the signal decrease is more than compensated by an improvement in the noise (from 0.3567 nC to 0.0286 nC). The limits of detection calculated as 3× multiples of noise improve by a factor of 4-6 (for example LOD of ethanol 4×).

EXAMPLE 5

Improved Linearity

Figure 7:
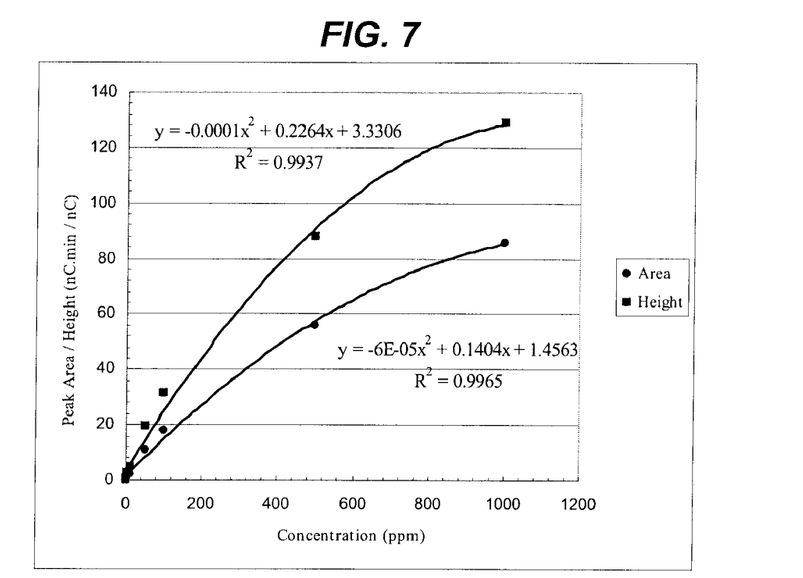
FIG. 7 shows calibration curves for ethanol by the prior art method (Signal integration at E1)(see waveform in FIG. 1).

The plot of FIG. 7 shows calibration curves for ethanol by the prior art method (Signal integration at $E1$ (see waveform in FIG. 1).

Figure 8:
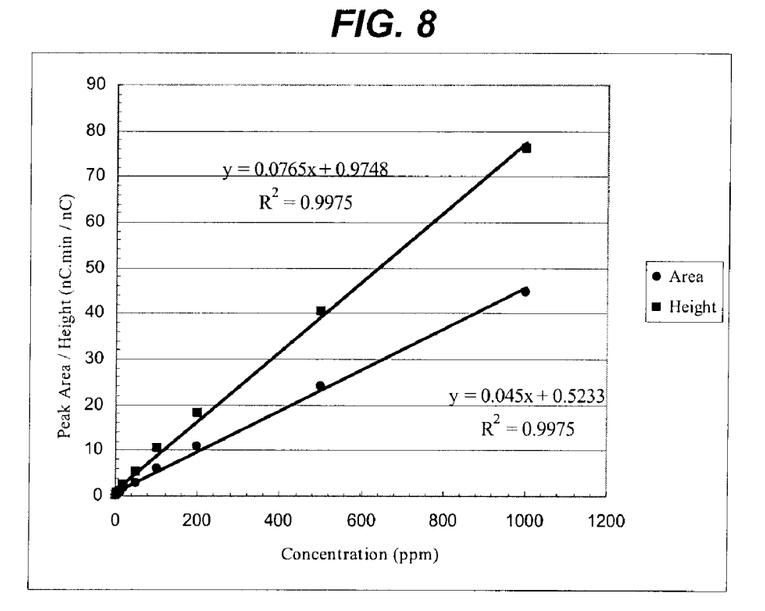
FIG. 8 shows data for ethanol obtained by signal integration at the highest potential of the waveform (see E2 in waveform of FIG. 2).

In the plot of FIG. 8, the data for ethanol was obtained by signal integration at the highest potential of the waveform (see $E2$ in waveform of FIG. 2).

The linearity of calibration is clearly improved by signal integration at the highest potential of a waveform.

Figure 9:
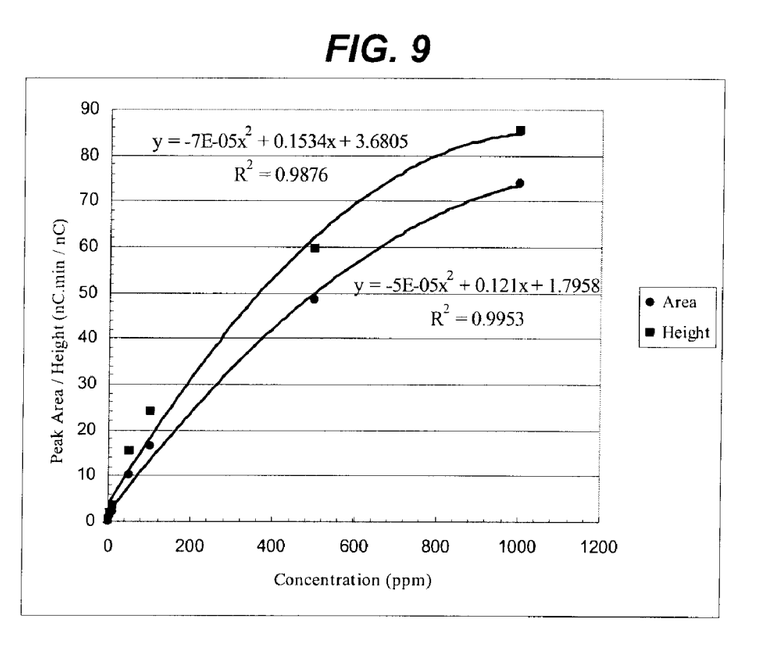
FIGS. 9 and 10 show the linearity improvement for 1-propanol.
Figure 10:
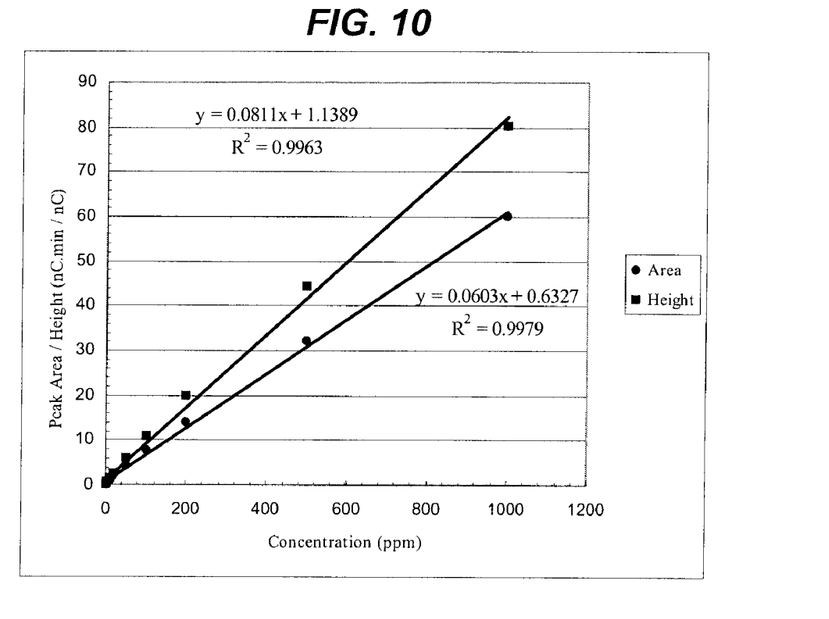

The plots of FIGS. 9 and 10 show the linearity improvement for 1-propanol.

EXAMPLE 6

Detection of Compounds with Double Bonds

Figure 11:
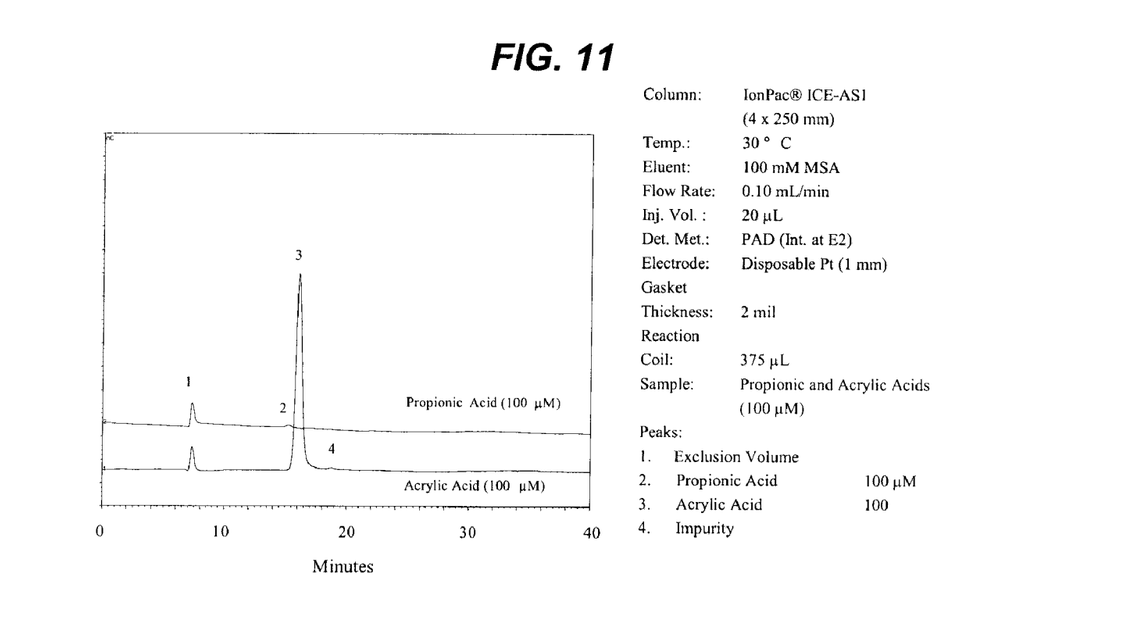
FIG. 11 shows a detection of saturated and unsaturated organic acids.

FIG. 11 shows a detection of saturated and unsaturated organic acids.

Propionic acid has the same number of carbon atoms and a carboxyl as the acrylic acid. The acrylic acid differs only in having a double bond. The higher detection signal in the lower of the two traces is explainable by oxidation of the double bond of acrylic acid at the platinum electrode.

EXAMPLE 7

Detection of Compounds with Triple Bonds

Figure 12:
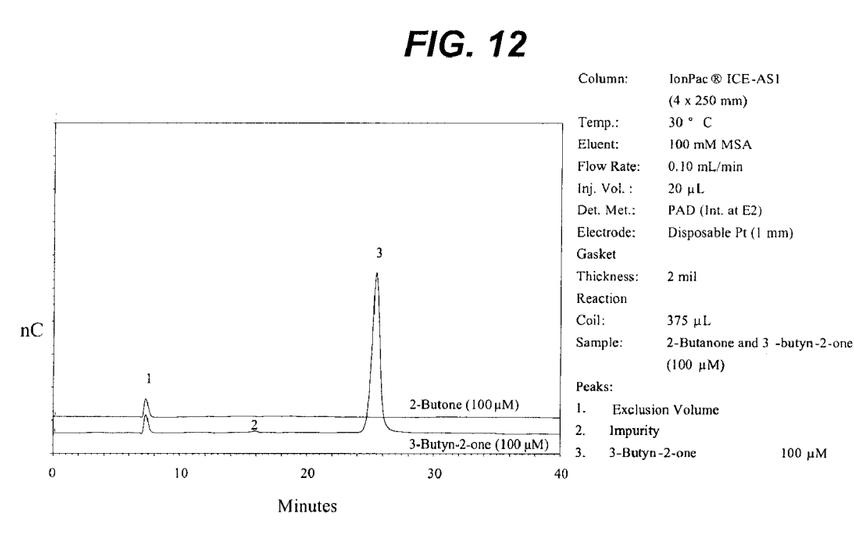
FIG. 12 shows a detection of triple bond in an organic compound.

FIG. 12 shows a detection of triple bond in an organic compound.

Butanone and 3-butyn-2-one posses the same number of carbon atom and the same ketonic group. 3-butyn-2-one differs only in the additional triple bond. The higher detection signal in the lower of the two traces is explainable by an oxidation of the triple bond of 3-butyne-2-one at the platinum electrode.

Table 1 provides a list of all compounds and compound classes that are now detectable with platinum electrodes. Two new compound classes have been made accessible to electrochemical detection (ethers and ketones). Sensitivity of detection was improved for all compounds listed in the table.

TABLE 1

| Compound class | Detected & reported by prior art | Detectable but unreported by prior art | Undetectable by prior art | Detectable by new method | New method improves LOD | Comments |
| --- | --- | --- | --- | --- | --- | --- |
| Inorganic anions | x | x(*) |  | x | x | Sulfite, peroxide, azide*, cyanide*, iodide, thiocyanate, iodate, arsenite, bromide, molybdate |
| sulfur AA | x |  |  | x | x | Only cysteine reported |
| thioethers |  | x |  | x | x |  |
| sulfoxides |  | x |  | x | x |  |
| alcohols | x |  |  | x | x | also carbohydrates |
| phenols | x |  |  | x | x | also catecholamines |
| ethers |  |  | x(**) | x |  | **some ethers are detectable, i.e. methoxy |
| aldehydes | x |  |  | x | x |  |
| ketones |  |  | x | x |  |  |
| alkenes |  | x |  | x |  |  |
| alkynes |  | x |  | x |  |  |
| nitriles |  | x |  | x |  |  |
| carboxylic acids | x |  |  | x | x |  |

*indicates inorganic anions which are detectable by the prior art methods but remained unreported. Their detection on platinum electrodes is described here for the first time.
**qualifies the statement about ethers being undetectable by the prior art method. A subset of ether group, methoxy compounds, can be detected by prior art.

What is claimed is:

1. A pulsed electrochemical detection method comprising the steps of (a) flowing a liquid sample stream including at least one analyte past a working electrode in a flow-through cell;

(b) applying at least three pulsed electrical potentials to said working electrode, (1) a first conditioning potential, (2) a second detection and oxidative cleaning potential, and (3) a third reductive cleaning potential, said second potential being higher than said first and third potentials and said first potential being higher than said third potential; and (c) detecting the output from said working electrode during at least part of the time period of applying said second potential.

2. The method of claim 1 in which said working electrode has an exterior surface formed of a material selected from the group consisting of platinum, iridium, palladium, rhodium, ruthenium, and lead.

3. The method of claim 2 in which said working material exterior surface is platinum.

4. The method of claim 1 in which said output is not detected during the time period of applying said first or third potential.

5. The method of claim 1 in which said flow-through cell is a two-electrode cell including a reference electrode and a working electrode.

6. The method of claim 1 in which said flow-through cell is a three-electrode cell and one of said three electrodes is a reference electrode.

7. The method of claim 1 in which said liquid sample stream includes at least one analyte, said method further comprising flowing said liquid sample stream through separation medium to separate said analytes to form separated analytes in said liquid sample, and detecting said separated analytes.

8. The method of claim 7 in which said separation is performed by liquid chromatography.

9. The method of claim 1 in which said analyte includes one or more compounds selected from the group consisting of inorganic anions, alcohols, sulfur amino acids, thioethers, sulfoxides, phenols, ethers, aldehyes, ketones, alkenes, alkynes, nitriles, amino acids and carboxylic acids.

10. The method of claim 1 in which said detecting is performed by current integration.

11. The method of claim 1 in which said detecting is performed amperometrically.

12. The method of claim 1 in which the external surface of the working electrode includes a surface oxide during application of the second potential and is in an oxide free state during application of the third potential.

13. The method of claim 1 in which said first potential is applied at least in part in a potential sweep function.

14. The method of claim 1 in which said first potential is applied at least in part in a potential step function.

* * * * *